(12) United States Patent
Karapetyan

(10) Patent No.: US 7,377,781 B1
(45) Date of Patent: May 27, 2008

(54) MOLAR DENTAL IMPLANT

(76) Inventor: Armen Karapetyan, 1935 N. Van Ness Ave., Los Angeles, CA (US) 90068

(*) Notice: Subject to any disclaimer, the term of this patent is extended or adjusted under 35 U.S.C. 154(b) by 211 days.

(21) Appl. No.: 11/324,900

(22) Filed: Jan. 4, 2006

(51) Int. Cl.
*A61C 8/00* (2006.01)

(52) U.S. Cl. ............... 433/173; 433/172; 433/174

(58) Field of Classification Search ........... 433/171, 433/173, 174, 18, 225, 175, 176
See application file for complete search history.

(56) References Cited

U.S. PATENT DOCUMENTS

| | | | |
|---|---|---|---|
| 4,468,200 A | * | 8/1984 | Munch ............... 433/174 |
| 4,547,157 A | * | 10/1985 | Driskell ............. 433/173 |
| 4,746,293 A | | 5/1988 | Lundgren et al. |
| 5,205,746 A | * | 4/1993 | Chanavaz ........... 433/174 |
| 5,542,847 A | | 8/1996 | Margulies |
| 7,293,991 B1 | * | 11/2007 | Karapetyan ......... 433/173 |
| 2004/0096804 A1 | * | 5/2004 | Vogt et al. .......... 433/173 |

* cited by examiner

*Primary Examiner*—John J Wilson
*Assistant Examiner*—Hao D Mai

(57) ABSTRACT

The improved molar and/or pre-molar dental implant embedded in the bone of a person's (a dental patient's) jaw prevents a possibility of the implant's pivotability into the extracted tooth socket after insertion. An improved dental implant includes an upper portion, a basis and a lower portion of the implant's body. The upper portion comprises a main neck, a rim and a conic rhomboid form head, including an aperture comprising an inner thread. The lower portion includes a rod comprising the plurality of extensions, and a transverse space crossing the rod along its lateral axis.

3 Claims, 3 Drawing Sheets

24-24

MOLAR DENTAL IMPLANT

FIELD OF THE INVENTION

This invention relates to a dental tooth implants and, more particularly, to molar and/or pre-molar (jewing) tooth implant embedded in the bone of a person's (a dental patient's) jaw.

BACKGROUND OF THE INVENTION

Some kind of a simple implantation of teeth in the mouth is known from the Pharaoh's ancient times. Modern dental surgical tooth implantation are extremely efficient. Various embodiments of oral implants are known, these commonly including a tubular body consisting of a smooth head and a cylindrical or cylindro-conical rod intended to be screwed or inserted by compaction into an osseous volume drilled beforehand using a tap. The firsts ancient osseointegration techniques was poor and the attachments for the implants in the jaw bone were purely mechanical and were not as successful as the present techniques that rely on osseointegration. However, it is known that before osseointegration, it was not necessary to wait for prolonged time periods until integration was completed. Some known prior art provides the means for attachment of an implant to the jaw bone structure by means of pins that are forced laterally out from the implant after the implant is inserted in the bone. These pins have pointed ends that, with application of high force, penetrate the bony structure, i.e., the softer spongiosa of the jaw bone, in an effort to make a tooth implant permanent. However, the spongiosa is a relatively soft, living bony material, and subject to changes. Accordingly, reliability and permanence of an implant were not assured. Another known procedure of the missing tooth replacement is to open the gum and to embed an implant in the bone structure beneath the gum. The implant is held in the bone in a socket hole by friction or the implant may be threaded into the bone. The gum is then closed over the implant and heals. When a proper material is used for the implant, e.g., titanium, the bone grows into the implant by osseointegration so that after several months the implant becomes a part of the bone structure in the mouth. The procedures, which are followed after osseointegration has advanced, depends upon the dental practitioner's selection of a manufacturer's product. The mentioned above complete systems of dental implants and prostheses for subsequent attachment to the implants are well known and described, for example, a system that is widely used by dental practitioners is available from Nobelpharma USA Inc., Westmont, Ill. In one system, the implant in a typical construction has an axially threaded hole at its top, i.e., the proximal end near the gum. After the bone has joined to the implant, the gum over the implant is reopened to expose the tapped hole. Then, an abutment is threaded into the tapped hole of the implant and extends to a level above the gum. The protruding end of the abutment is constructed with a non-round shape for attachment of a prosthesis. Also, the protruding end includes a central threaded hole extending inward toward the jaw bone. A false tooth or crown is provided with a hole, known as a chimney, therethrough, and a non-round recess in its base that corresponds in shape to the protruding non-round cross-section of the abutment. Thereby, the crown can be joined to the abutment with a self-aligning connection that prevents relative rotation between them. A screw, passed into the chimney opening, engages the tapped hole in the abutment so as to hold the crown axially to the abutment. Thus, the crown cannot rotate about the abutment because it is fixed into the special contours on the exposed abutment end, and the crown cannot pull away from the abutment when the screw has been tightened in place. Finally, the chimney above the screw is filled with a composite filler material that hardens and is shaped as part of the crown, to look like a natural tooth.

However, the problem, and a source of patient dissatisfaction, resides in the several months of marked inconvenience for the patient while the process of osseointegration takes place and the implant becomes fixedly attached to the jaw bone. This difficulty, to be overcome, requires an avoidance of eating and chewing foods that will cause undesirable stresses and force transmissions in the tooth region. From present understanding, it appears that osseointegration takes place between the bone and the titanium implant under strict conditions of immobilization and without force or stress applied on the bone/implant interface. An uninterrupted growth of bone on the titanium surface is the time-consuming factor. It is not completely clear at this time whether osseointegration taken place under the condition of extreme immobilization and, if not, how much movement of the implant is tolerable. It is also not clear whether controlled application of force is harmful, or may actually help if applied in a specific manner. From many years of metal implantation in bones, it has been learned that stress sharing constructions made of bone and implant encourage bone healing and bone growth, while stress shielding implants prevent healing, mainly by eliminating the stimuli from the body's osteoblasts. After a tooth extraction, it is necessary that the site should heal prior to initiating implant procedures. This further extends the time period until the patient is ready to resume normal chewing at the site.

What is needed is an implant system that provides effective attachment to the bone in a shorter period of time than present implants require, and with less inconvenience for the patient during the period when osseointegration takes place.

For example, the U.S. Pat. No. 5,542,847 describes the dental prosthesis implants placed into a socket formed in the jaw bone, is held in position by screws that pass through the jaw bone from the buccal cortical surface to the lingual cortical surface, and through the implant that is located between the cortical surfaces. Threads on the screw shank form and engage threads in the cortex on opposite sides of the jaw bone. The implant, when inserted in the socket and anchored by the screws, is strongly held to the jaw's bony structure. Stresses applied to a prosthetic device, e.g., a tooth crown that is attached to the implant, are substantially borne by the cortex by way of the screws.

Despite of strong connection, such implant installation requires additional alien subjects (e.g. the screws passing through the jaw bone from the buccal cortical surface to the lingual cortical surface) in the human (patient's) jaw, that is highly discomfortable and also requires longer time for the patient's recovery.

Another implants and the connecting device are disclosed in U.S. Pat. No. 4,746,293. The patent describes an implant with the individual crowns, preventing possible torsional forces from running up and disengaging the spacer screw with a milled groove in which a droplet of acrylate is applied for reversible locking. Generally, the implant and connecting device comprise an anchorage unit (a fixture) implanted in jawbone tissue. The spacer is provided with a central, cylindrical spacer screw designed specifically for this purpose with an extended, exteriorly threaded pin. The spacer is provided with a collar consisting of two surfaces: an outer horizontal surface and an obliquely inclined surface located inside the surface.

The anchorage unit and the outer prosthesis portion, a connecting device in the form of an outer, sleeve-shaped patrix is connected to the spacer. The outer circumferential surface of the patrix connects to the outer prosthesis portion and the patrix surrounds the central spacer screws. The base of the patrix is connected to the collarshaped portions of the spacer by the intermediary of a resilient member in the form of a rubber O-ring.

The obliquely inclined surface of the collar-shaped portion of the spacer forms, together with an upper horizontal surface 8 on a cuff of the spacer, two of the walls of an annular tunnel for the resilient member, namely the lower horizontal wall and the oblique lateral wall. The remaining walls of the annular tunnel viz. the medial, vertical wall and the upper horizontal wall are formed by the circumferential surface of the spacer screw, which in this case is of circular profile, and the planar, lower base surface of the patrix, respectively.

The annular tunnel of rhomboid cross-section which is formed by the above-mentioned surface is adapted to the resilient member in the form of an O-ring of rubber. The O-ring is dimensioned to permit a deflection of the order of magnitude of about 100-200 nu.m. In eccentric or oblique loading, this corresponds to a maximum angular displacement of 1°-2°.

The patrix surface is so disposed as to depress the O-ring and provide the contemplated elastic transmission of forces between the outer prosthesis portion and the spacer (the fixture). The play provided between the patrix surface and the spacer collar surface should exceed 200 nu.m in order to permit the planned elastic deflection of 100-200 nu.m.

The elastic connection is anchored (locked) by an interiorly threaded special nut manufactured of, for example, gold. The nut is screwed onto the exteriorly threaded pin of the spacer screw such that its lower peripheral end surface meets a horizontal heel on the patrix. The nut is screwed on so far that light compression of the O-ring is attained. This light compression or pre-tensioning may be exactly determined in that the screw which is disposed in the top of the nut is turned so as to register with a groove in the upper patrix edge. By provision of further two such groove markings in the patrix edge to which the screw slot can be turned, both moderate and hard pre-tensioning of the connecting device may be mode, depending upon the deflection amplitude which is deemed to be most purposeful in each individual situation.

The upper surface of the special nut may be covered with, for example, a gold washer once it has been locked by a droplet of acrylate. Acrylate is then applied over the gold washer in order to fill the aperture through which the nut was applied.

The implant with such connection is not sufficiently reliable considering the presence of the rubber O-ring.

Thus, there is a great need in the art for the improved not complex, not expensive and reliable molar and/or pre-molar dental implant embedded in the bone of a person's (a dental patient's) jaw.

OBJECT AND ADVANTAGES OF THE INVENTION

Accordingly, several objects and advantages of the present invention are to provide reliable not complex and not expensive molar/pre-molar dental implant.

It is another object of the invention to provide the implant's upper portion configuration preventing the artificial tooth pivotability around the implant.

It is still another object of the invention to provide the implant's lower portion elongated configuration preventing the implant pivotability into the socket (into an osseous plate, in which an implant has been osteo-integrated in) after implant's insertion.

It is yet another object of the invention to provide the universal possibility to use an osteointegrated implant for rigid connection with the artificial tooth (e.g.: by a screw, etc.) or for connection providing the artificial tooth removability (e.g.: a clamping device, etc.).

Still, further objects and advantages will become apparent from a consideration of the ensuing description accompanying drawings.

DESCRIPTION OF THE DRAWING

In order that the invention and the manner in which it is to be performed may be more clearly understood, embodiments thereof will be described by way of example with reference to the attached drawings, of which.

SUMMARY OF THE INVENTION

Most known molar/pre-molar dental implants are complex and have cylindrical configuration of their bodies, that creates a possibility of the implant's pivotability into the extracted tooth socket after insertion.

Thus, there is a great need in the art for the improved not complex, not expensive and reliable molar and/or pre-molar dental implant embedded in the bone of a person's (a dental patient's) jaw.

An improved molar/pre-molar dental implant (hereinafter will be mentioned as "dental implant" or "implant") includes an upper portion, a basis and a lower portion of the implant's body. The upper portion comprises a main neck, a rim and a conic rhomboid form head, including an aperture comprising an inner thread. The lower portion includes a rod comprising an outer thread, and a transverse space crossing the rod along its lateral axis.

DESCRIPTION OF THE PREFERRED EMBODIMENTS

Herein the description of an improved dental implant will be done in statics (as if the components of the improved device are suspended in the space) with the description of their relative coupling to each other. The description of the functional operations of the improved dental implant will be done hereinafter.

Figure 1:
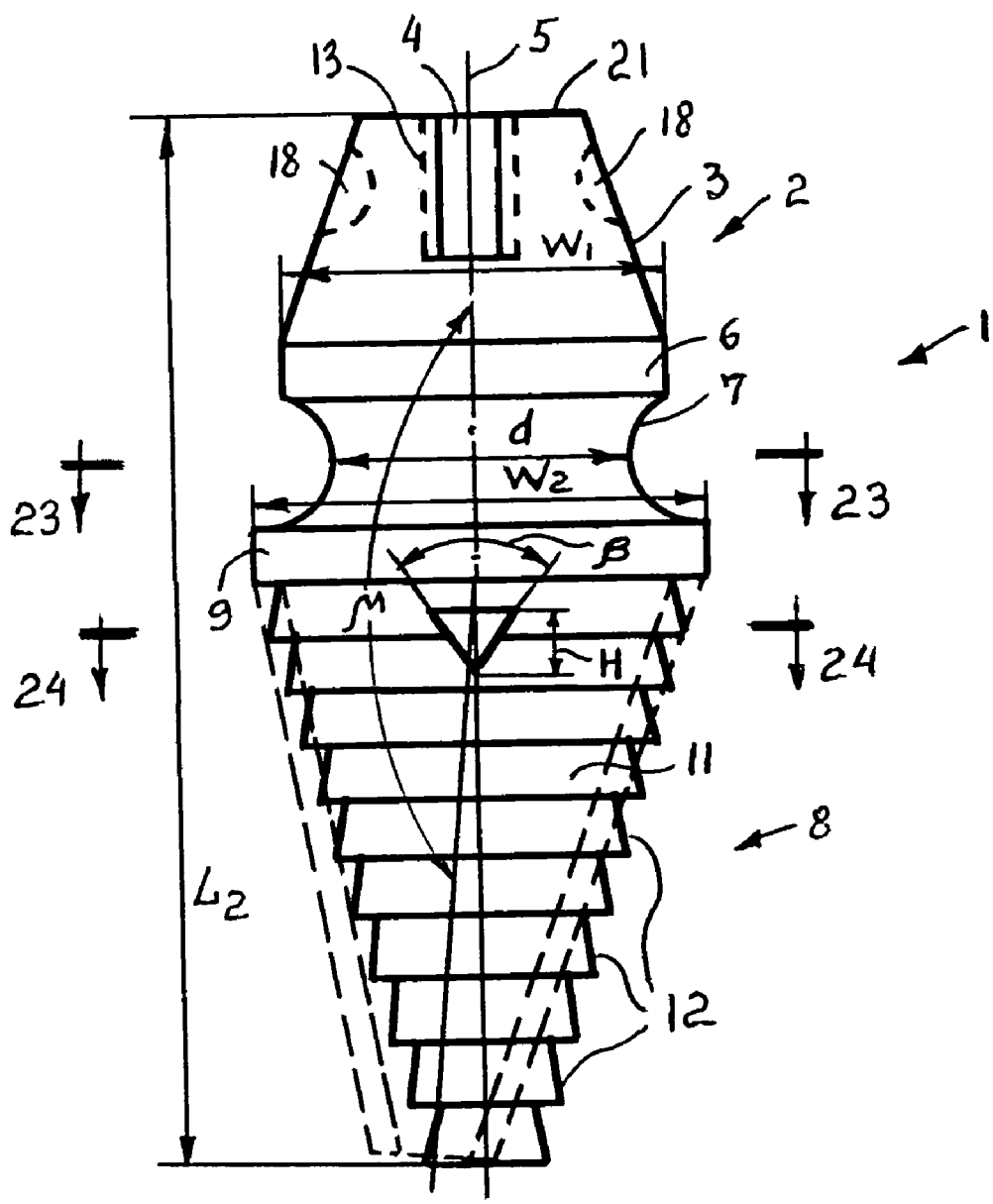
FIG. 1 is a simplified drawing of the improved molar/pre-molar dental implant.
Figure 2:
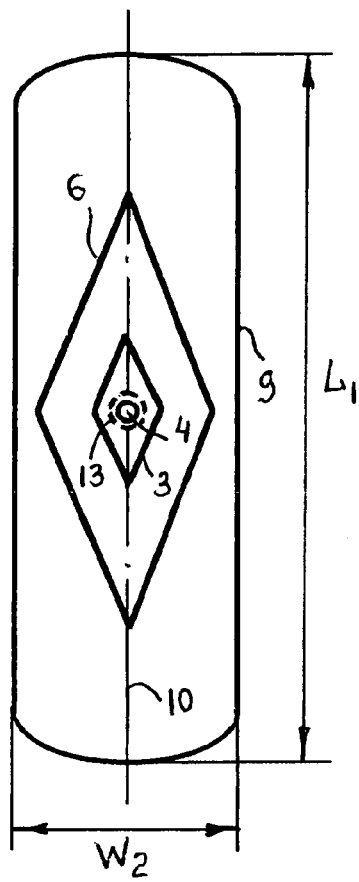
FIG. 2 is a simplified top view of the improved molar/pre-molar dental implant.
Figure 3:
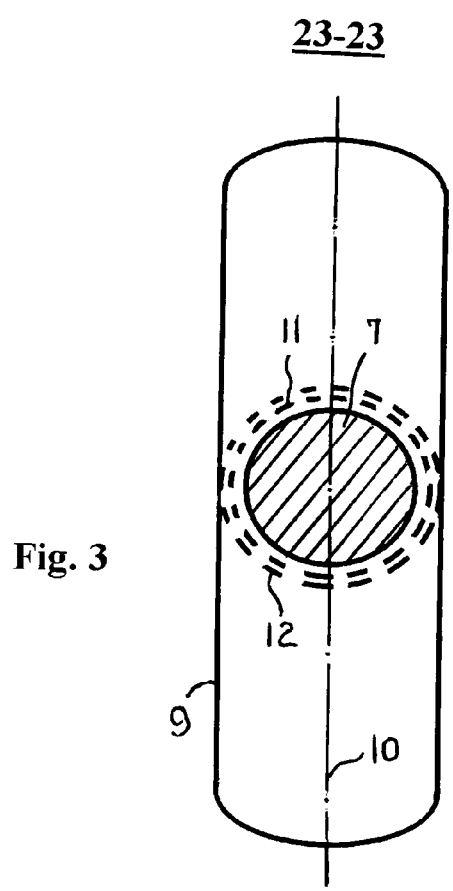
FIG. 3 is a cross-sectional view 23-23 of the improved molar/pre-molar dental implant.
Figure 4:
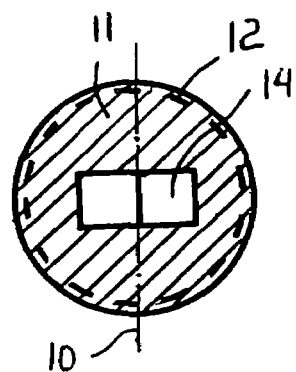
FIG. 4 is a cross-sectional view 24-24 of the improved molar/pre-molar dental implant.

An improved dental implant, referring to FIG. 1, includes a body 1 comprising an upper portion 2 including a head 3 (preferably of conic shape of the rhombic configuration, i.e.

conic rhomboid, as it is shown in FIG. 2) comprising an aperture 4 of a cylindrical shape. The aperture 4 is located longitudinally along the longitudinal (vertical) axis 5 of the body (dental implant) 1 and includes an inner thread 13. The head 3 can be of any regular geometrical shape/form and/or configuration, for example, of square, elliptical form, etc. or of any irregular form, for instance, squared-barrel form, etc. The preferred non-circular form of the head 3 of the improved implant(s) prevents the artificial tooth pivotability around the implant (implant's head).

Also, the upper portion 2 includes rim 6 and the main neck 7 in the form of cylindrical groove. The diameter "d" of the main neck (groove) 7 is smaller than the width "$W_1$" of the rim 6. The upper portion 2 is "conventionally separated" from the lower portion 8 by the basis 9. The dental implant (body 1) is an entire (solid) piece comprising the lower portion 8, basis 9 and the upper portion 2. The basis 9 has an elongated configuration and is elongated along the implant's lateral axis 10. The basis 9 is preferably of the rectangular form with the rounded two smaller sides of the rectangle, as shown in FIG. 2. The basis 9 also can be of any reasonable configuration/form/shape, for example, of elliptical form, etc. The width "$W_2$" of the basis 9 is bigger than the diameter "d" of the main neck 7, and bigger than the width "$W_1$" of the rim 6 ($W_2 > W_1 > d$). The rim 6 can for example be of rhombic form, as it is shown in FIG. 2. The lower portion 8 comprises a rod 11 preferably of the conic configuration, as shown in FIG. 2, but the rod 11 can be of any reasonable configuration, for instance, of a cylindric form, etc. The rod 11 includes an extensions 12 (shown in FIG. 1) and the transverse triangular space (triangular hole, triangular aperture) 14, crossing the threaded rod 11 along the lateral axis 10. The transverse triangular space 14 can cross the rod 11 along any transverse axis (not shown) around 360° along the lateral (horizontal) plane. The angle "β" can be of any degree and preferably in the range of 30°-70° (in FIG. 1, the angle "β" is shown at approximately 60° [β≈60°]). The traverse space 14 can be of any regular or irregular geometrical form, for example, of square, elliptical, rectangular form, etc. The transverse space 14 provides a blood irrigation additionally to the blood passage via lower portion 8 circumference. As known, it thus contributes locally to maintaining the physiological equilibrium of the blood. It therefore counters the corresponding increase in acidity of the bone in this zone, and thus its becoming brittle. The blood passage in the space 14 thus returns the calcium content of the bone to normal. Such space also promotes the genesis of a bone "cortex" through the space 14, which contributes to the blocking (or natural wedging) of the implant, and prevents the implant's pivoting in the bone socket after insertion. Additionally, as known from the dental practice it limits the progress of the dehiscence or resorption of the bone, as it is found in all the known implants after a period of the order of 5 to 7 years, by maintaining an osseous zone protected in the space 14.

The triangular space 14 is thus an element providing the stronger osseous destruction around the implant, and is an element for its biomechanical reinforcement.

The lower portion 8 is by the threaded rod 11 installed (osteo-integrated) into the socket (extracted natural tooth cavity). More specifically, the threaded rod 11 is screwed into a jaw's bone (an osseous plate) 16 of the patient's jaw 17, and is extended over the gum by the upper portion 2 of the implants' 1 in order to be coupled with a prosthetic structure (artificial tooth) 15. The coupling of the artificial tooth 15 with the implant 1 can be provided by an appropriate screw (not shown) passing along the threaded aperture 4 preferably located in the center of the upper surface 21 of the head 3 of the upper portion 2 of the body (implant) 1.

The lower portion 8 can be slightly biased of the longitudinal axis 5, and can be at the angle "μ" to the upper portion 2, as it is shown in FIG. 1. Practically, the angle "μ" can be in the range from about 175° to 180° (μ≈175-180°).

The upper portion 2 is located outside of the jaw 17 for crown 15 attaching, and the lower portion 8 with the basis 9 are located in the jaw's socket.

Figure 5:
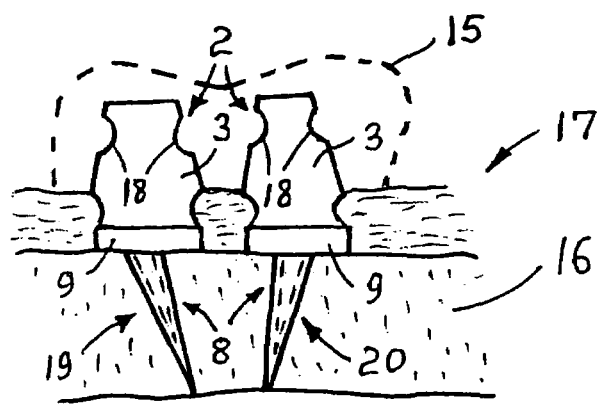
FIG. 5 is a simplified drawing of the molar dental multi-implant insertion variant.
Figure 6:
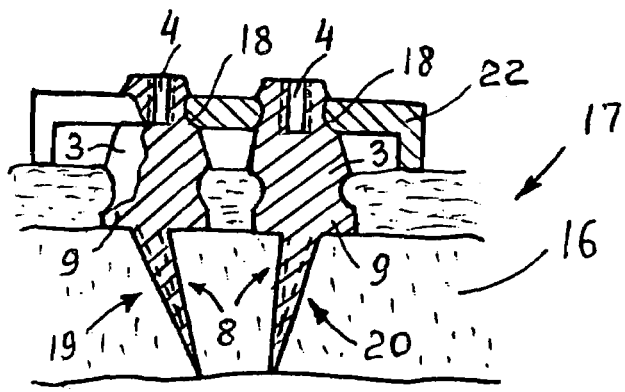
FIG. 6 is a simplified drawing of the molar dental multi-implant fixing.

The single implant (body) 1 can be for example used for pre-malar teeth. In this case the straight implant (μ=180°) is mostly used. Two implants can be used for the malar teeth, if needed, as shown in FIG. 5. For this case, two implants (bodies): a first implant 19 and a second implant 20 are inserted into the extracted natural malar tooth socket, and the single artificial tooth (crown/veneer) 15 can be appropriately coupled with them, for instance, by two screws (not shown). The angle "μ" for each of two implants 19, 20 can be less than 180° (μ<180), as it is shown in FIG. 6, and be preferably in the mentioned above range. The head 3 of each implant 19 and 20 can include the auxiliary neck 18, providing leveling and fixing of the implanted bodies 19 and 20 by a fixing means 22, for example shown in FIG. 6. The fixing means 22 comprises two halves (not shown) coupled to each other, but can be of any reasonable principles (e.g. twisted "wires"/not shown/, etc.) and configuration, and not limited by the fixing means presented (as an example) in FIG. 6.

The width "$W_2$" can for example be about 3 mm ($W_2 \approx 3$ mm), "$W_1$" can be 2 mm ($W_1 \approx 2$ mm), and diameter "d" can be about 1.5 mm (d≈1.8 mm). The height "H" of the triangular trans-verse space 14 can be about 2 mm (H≈2.0 mm), and can be located approximately 1.5 mm-2 mm below the basis 9. The length "$L_1$" of the basis 9 can be about 4 mm (L≈4 mm), and the length "$L_2$" of the body 1 can be about from 8 mm to 14 mm ($L_2 \approx 8$-14 mm). All presented dimensions can vary depending on the reasonable unification aspect in the dental implant industry, and/or some other reasonable factors, e.g.: patient's natural teeth unique size, etc.

The extensions 12 (located around the rod 11) can be of any form, for example, a circular triangular form, as it is shown in FIG. 1, or a circular isosceles-trapeziumic configuration, etc.

It should be understood that the above description discloses specific embodiments of the pre-sent invention and are for purposes of illustration only without any limitations. There may be other modifications and changes obvious to those of ordinary skill in the art which fall within the scope of the present invention.

CONCLUSION, RAMIFICATION AND SCOPE

Accordingly the reader will see that, according to the invention, I have provided the improved dental implant. The improved dental implant has various possibilities, considering activities and applications of the implanted dental teeth.

While the above description contains many specificities, these should be not construed as limitations on the scope of the invention, but as exemplification of the presently-preferred embodiments thereof. Many other ramifications are possible within the teaching to the invention. For example, the improved dental implants can easily be applicable for inserting in the front (nasal) mouth areas too, etc.

Thus, the scope of the invention should be determined by the appended claims and their legal equivalents, and not by examples given.

THE DRAWING REFERENCE NUMERALS

1. —a body (an implant);
2. —an upper portion;
3. —a head;
4. —a threaded aperture;
5. —a longitudinal axis;
6. —a rim;
7. —a main neck;
8. —a lower portion;
9. —a basis;
10. —a lateral axis;
11. —a rod;
12. —an extension;
13. —an inner thread,
14. —a transverse space;
15. —an artificial tooth (crown);
16. —a jaw's bone (osseous plate);
17. —a jaw;
18. —an auxiliary neck;
19. —a first implant;
20. —a second implant;
21. —an upper surface;
22. —a fixing means;
23-23 is a cross-sectional view;
24-24 is a cross-sectional view.

What is claimed is:

1. An improved molar/pre-molar dental implant comprising a solid body including
   an upper portion intended for a coupling with a crown and comprising
      a conic rhomboid head including an aperture, the aperture located along a longitudinal axis of said body, in a center of an upper surface of said conic rhomboid head, and wherein said aperture includes an inner thread for said coupling with said crown;
      a rhombic form rim located in a bottom portion of said conic rhomboid head, wherein the rhombic form rim has a width;
      a main neck located in a bottom portion of said rhombic form rim and having a diameter smaller than the width of said rhombic form rim;
      a basis of elongated form located in a bottom portion of said main neck, and wherein said basis has a width which is bigger than said width of said rhombic form rim;
   a lower portion extended from said basis and including
      a conic form rod located along said longitudinal axis and intended for insertion into a socket of the extracted tooth, and wherein said conic form rod comprises a plurality of extensions;
      a transverse triangular space crossing said conic form rod along the lateral axis, and wherein said transverse triangular space is located in an area of said basis.

2. The dental implant of claim 1, wherein said conic rhomboid head further includes an auxiliary neck located in an upper area of said conic rhomboid head.

3. The dental implant of claim 1, wherein said conic form rod is further located under angle to said upper portion which is located along said longitudinal axis.

* * * * *